(12) United States Patent
Kassab (10) Patent No.: US 10,219,828 B2
(45) Date of Patent: Mar. 5, 2019

(54) DEVICES, SYSTEMS, AND METHODS FOR TRANSRADIAL ACCESS

(75) Inventor: Ghassan S. Kassab, Zionsville, IN (US)

(73) Assignee: DTherapeutics, LLC, San Diego, CA (US)

( * ) Notice: Subject to any disclaimer, the term of this patent is extended or adjusted under 35 U.S.C. 154(b) by 227 days.

(21) Appl. No.: 13/283,024

(22) Filed: Oct. 27, 2011

(65) Prior Publication Data

US 2012/0108926 A1     May 3, 2012

Related U.S. Application Data

(60) Provisional application No. 61/407,211, filed on Oct. 27, 2010.

(51) Int. Cl.
| | |
|---|---|
| *A61B 17/34* | (2006.01) |
| *A61B 17/00* | (2006.01) |
| *A61B 5/053* | (2006.01) |
| *A61B 5/145* | (2006.01) |

(52) U.S. Cl.
CPC ........ *A61B 17/3403* (2013.01); *A61B 5/0538* (2013.01); *A61B 5/14542* (2013.01); *A61B 5/14546* (2013.01); *A61B 17/3496* (2013.01); *A61B 2017/00026* (2013.01); *A61B 2017/00867* (2013.01); *A61B 2017/00907* (2013.01); *A61B 2017/3405* (2013.01)

(58) Field of Classification Search
CPC ............ A61B 17/3403; A61B 17/3496; A61B 2017/3405; A61B 5/0538; A61B 5/14546; A61B 5/14542; A61B 2017/00867; A61B 2017/00907; A61B 2017/00026; A61B 17/3401; A61B 17/3409; A61B 17/3415; A61B 17/3474; A61B 17/3494
USPC ....... 606/185, 108, 159, 167, 170, 184, 213, 606/214; 600/323, 309, 547; 604/164.08
See application file for complete search history.

(56) References Cited

U.S. PATENT DOCUMENTS

| | | | |
|---|---|---|---|
| 2003/0229353 A1* | 12/2003 | Cragg ............................ 606/86 |
| 2006/0111629 A1* | 5/2006 | Field et al. ................... 600/420 |
| 2007/0010843 A1* | 1/2007 | Green .......................... 606/185 |
| 2007/0191736 A1* | 8/2007 | Alden .......................... 600/583 |
| 2007/0233225 A1* | 10/2007 | Rapacki et al. ............. 623/1.12 |
| 2007/0249922 A1* | 10/2007 | Peyser et al. ................ 600/365 |
| 2008/0021493 A1* | 1/2008 | Levaughn et al. ............ 606/181 |
| 2008/0262431 A1* | 10/2008 | Anderson et al. ......... 604/164.1 |
| 2008/0294111 A1* | 11/2008 | Tal .................... A61M 25/0097 604/165.01 |
| 2009/0118752 A1* | 5/2009 | Perez et al. ................... 606/181 |

(Continued)

*Primary Examiner* — David C Eastwood
*Assistant Examiner* — Tin Nguyen
(74) *Attorney, Agent, or Firm* — Reichel Stohry LLP; Mark C. Reichel; Natalie J. Dean (57) ABSTRACT

Devices, systems, and methods for transradial access. In at least one embodiment of a device for providing access to a vessel or other luminal organ of the present disclosure, the device comprises a needle having a needle tip, a sheath positioned around at least part of the needle, the sheath defining an aperture at a distal sheath end, and a protractor in communication with the needle, whereby engagement of the protractor causes the needle tip to protract from the sheath, and whereby release of the protractor causes the needle tip to retract into the sheath.

17 Claims, 7 Drawing Sheets

(56) References Cited

U.S. PATENT DOCUMENTS

2009/0143737 A1\*  6/2009  Kobayashi ............ A61M 5/158
                                                              604/164.08
2011/0054390 A1\*  3/2011  Searle ................. A61M 5/1413
                                                              604/66

\* cited by examiner

DEVICES, SYSTEMS, AND METHODS FOR TRANSRADIAL ACCESS

PRIORITY

The present application is related to, and claims the priority benefit of, U.S. Provisional Patent Application Ser. No. 61/407,211, filed Oct. 27, 2010, the contents of which are hereby incorporated in their entirety into the present disclosure.

BACKGROUND

Interventional procedures (including coronary angiography and angioplasty) are usually performed via transfemoral access. Although this route provides relatively easy vascular access, it is associated with several shortcomings.

First, such a route is difficult to implement with patients that have substantial peripheral artery disease (such as aortoileofemoral obstructive disease), abdominal aortic aneurysm, groin infection, or morbid obesity. Second, a small but potentially serious incidence of vascular complications at the puncture site that may result in significant groin hematoma, which could lead to necessary blood transfusions and/or require surgical repair.

A major advantage of the transfemoral route is puncturing the accessible and large caliber femoral arteries is relatively easy. Although first attempted two decades ago, the radial (transradial) approach is still more difficult to perform and has a higher failure attempt rate (1-9% in experienced hands) primarily due to the smaller size of the vessels, whereby the needle tip may over-perforate during the procedure. Accordingly, the transradial technique has a steep learning curve.

Accordingly, alternative methods, and devices for performing transradial access would be well received by interventional practitioners treating patients meeting one or more of the aforementioned criteria. As such, there is clearly a need for a needle access device that allows visualization of puncture through blood retrieval and that allows retraction of the needle tip to prevent overperforation.

BRIEF SUMMARY

In at least one embodiment of a device for providing access to a vessel or other luminal organ of the present disclosure, the device comprises a needle having a needle tip, a sheath positioned around at least part of the needle, the sheath defining an aperture at a distal sheath end, and a protractor in communication with the needle, whereby engagement of the protractor causes the needle tip to protract from the sheath, and whereby release of the protractor causes the needle tip to retract into the sheath. In another embodiment, wherein when the protractor is not engaged, the needle tip is positioned within the sheath. In yet another embodiment, at least part of the sheath is comprised of transparent material. In an additional embodiment, at least part of the sheath is comprised of translucent material.

In at least one embodiment of a device for providing access to a vessel or other luminal organ of the present disclosure, when the needle tip punctures a vessel or other luminal organ so that fluid within the vessel or other luminal organ is in communication with the needle tip, the fluid can also enter a lumen of the sheath and be detected within the sheath. In an additional embodiment, the protractor is selected from the group consisting of a button and a rotatable dial. In yet an additional embodiment, the sheath further comprises a tapered distal end. In another embodiment, the tapered distal end of the sheath is configured to allow blood or other bodily fluids to pass between an outside wall of the needle and the aperture so that the blood or other bodily fluids can be detected within the sheath.

In at least one embodiment of a device for providing access to a vessel or other luminal organ of the present disclosure, the device further comprises a needle mechanism in communication with the needle and the protractor, the needle mechanism operable to facilitate protraction and retraction of the needle tip from the sheath. In another embodiment, the needle mechanism is selected from the group consisting of a spring, a compliant polymer, a coil, a sponge, and a bladder. In yet another embodiment, the device further comprises one or more wire apertures defined therethrough, the one or more wire apertures configured to receive a wire. In an additional embodiment, the device further comprises a wire positioned through the one or more wire apertures, the wire configured to permit a second device to be delivered over the wire. In various embodiments, the wire comprises a guide wire.

In at least one embodiment of a method of accessing a mammalian bodily vessel of the present disclosure, the method comprising the steps of protracting a needle tip from a sheath of a device, puncturing a bodily vessel of a patient using the needle tip so that the needle tip accesses a lumen of the bodily vessel, and retracting the needle tip into the sheath of the device. In another embodiment, the step of retracting the needle tip is performed upon detection of a fluid from the bodily vessel within the sheath of the device. In yet another embodiment, the bodily vessel comprises a radial artery.

In at least one embodiment of a method of accessing a mammalian bodily vessel of the present disclosure, the method further comprises the step of advancing a wire through the device so that at least part of the wire is positioned within the lumen of the bodily vessel. In an additional embodiment, the method further comprises the step of removing all or part of the device from the patient, allowing at least part of the wire to remain within the lumen of the bodily vessel. In yet an additional embodiment, the method further comprises the step of advancing a second device over the wire so that at least part of the second device is positioned within the lumen of the bodily vessel. In another embodiment, the step of advancing a second device comprises advancing a second device selected from the group consisting of a catheter, catheters, a balloon catheters and a stent.

In at least one embodiment of a transradial heart catheterization method according to the present disclosure comprises the steps of protracting a needle tip from a sheath of a device, puncturing a radial artery of a patient using the needle tip so that the needle tip accesses a lumen of the radial artery, retracting the needle tip into the sheath of the device upon detection of blood from the radial artery within the sheath of the device, advancing a wire through the device so that at least part of the wire is positioned within the lumen of the radial artery, removing all or part of the device from the patient, allowing at least part of the wire to remain within the lumen of the bodily vessel, and advancing a catheter over the wire so that at least part of the second device is positioned within the lumen of the radial artery and at least a portion of the patient's heart.

In at least one embodiment of a system for providing access to a vessel or other luminal organ of the present disclosure, the system comprises a needle having a needle tip, a sheath positioned around at least part of the needle, the sheath defining an aperture at a distal sheath end, and an actuator in communication with the needle, whereby a first operation of the actuator causes the needle tip to protract from the sheath, and whereby a second operation of the actuator causes the needle tip to retract into the sheath. In an additional embodiment, the system further comprises a needle mechanism in communication with the needle and the actuator, the needle mechanism operable to facilitate protraction and retraction of the needle tip from the sheath. In yet an additional embodiment, the system further comprises a sensor coupled to the needle and operable to sense at least one bodily parameter. In another embodiment, the at least one bodily parameter comprises an impedance, an oxygen concentration, and a lactate concentration. In yet another embodiment, the system further comprises a wire coupled to the sensor and directly or indirectly coupled to the actuator, the wire capable of transmitting a signal from the sensor to the actuator.

In at least one embodiment of a system for providing access to a vessel or other luminal organ of the present disclosure, the system further comprises a processor operably coupled to the sensor, the processor operable to control actuation of the actuator. In another embodiment, and when the sensor senses a threshold bodily parameter, the processor operates to control actuation of the actuator to protract or retract the needle.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 1:
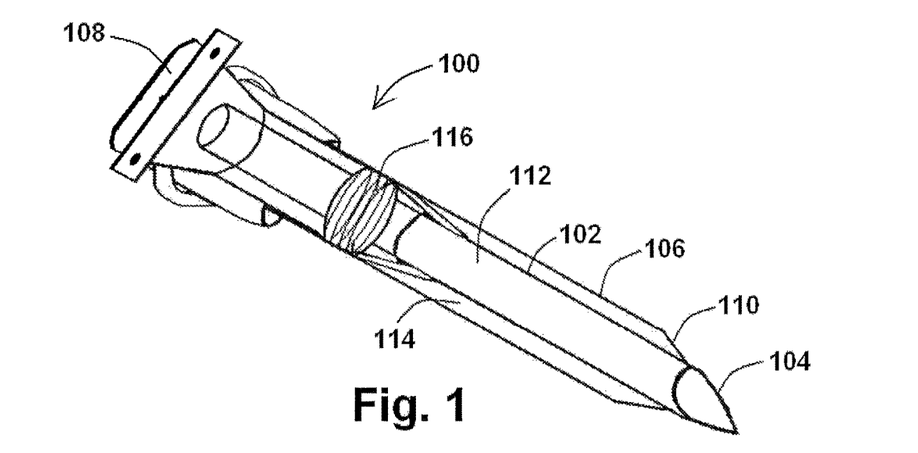
FIG. 1 shows a side view of a device for providing access to a vessel or other luminal organ in a first configuration, according to at least one embodiment of the present disclosure.
Figure 2:
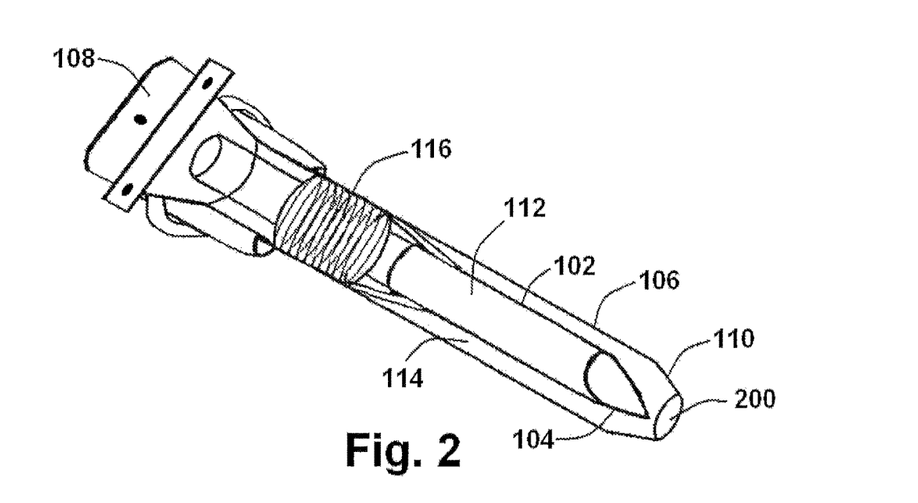
FIG. 2 shows a side view of a device for providing access to a vessel or other luminal organ in a second configuration, according to at least one embodiment of the present disclosure.
Figure 4:
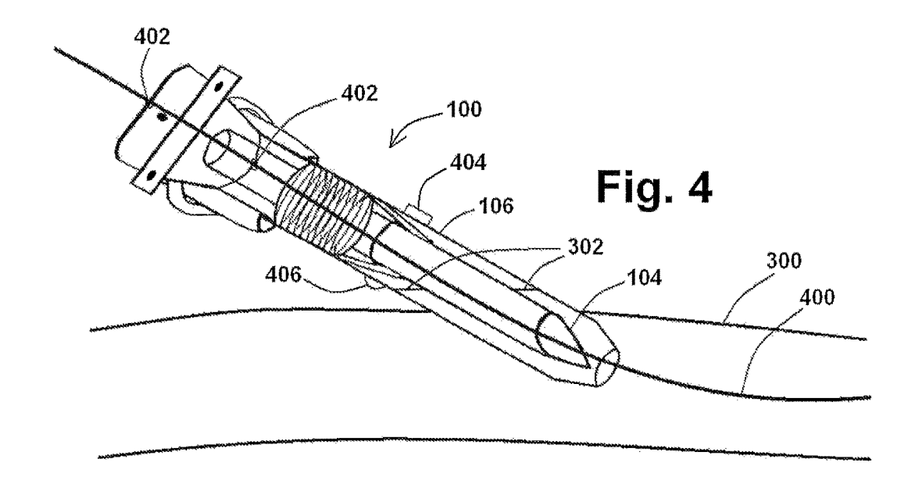
FIG. 4 shows a side view of a device for providing access to a vessel or other luminal organ in a second configuration and at least partially within a bodily vessel, according to at least one embodiment of the present disclosure.

An exemplary embodiment of an access device (which may be used to provide transradial access) according to the present disclosure is shown in FIGS. 1 and 2. As shown in FIGS. 1 and 2, device 100 comprises a needle 102 having a needle tip 104. Needle 102, as shown in FIGS. 1 and 2, may comprise the entire needle, or may comprise only a portion of a larger needle in at least another embodiment. Needle 102 is positioned at least partially within a sheath 106, whereby sheath 106 at least partially encircles needle 102 when at least part of needle 102 and needle tip 104 protrude from sheath 106 (an exemplary first configuration, as shown in FIG. 1), and whereby sheath 106 houses needle 102 and needle tip 104 when needle 102 is retracted within sheath 106 (an exemplary second configuration, as shown in FIG. 2). In at least one embodiment, sheath 106 may comprise a stopcock 404 and/or a valve 406, as shown in FIG. 4, to regulate pressure within sheath 106, for example, and/or to release air and/or a fluid from within sheath 106.

Device 100, as shown in FIG. 1 and in various embodiments, comprises a protractor 108 proximal to needle tip 104, wherein when protractor 108 is engaged, at least part of needle 102 and needle tip 104 protrude from sheath 106. Releasing protractor 108, as shown in FIG. 2, causes needle 102 and needle tip 104 to retract within sheath 106.

As shown in FIGS. 1 and 2, protractor 108 is a mechanism capable of being depressed and released, such as a physical button. However, additional embodiments of protractor 108 of the present disclosure may comprise any number of other suitable mechanisms, such as a rotatable dial, capable of causing at least part of needle 102 and needle tip 104 to protrude from and retract into sheath 106.

Sheath 106, in various embodiments of devices 100 of the present disclosure, is either completely or partially transparent or translucent, so that a user of device 100 can detect whether or not needle tip 104 has engaged a vessel, such as a blood vessel, to an extent that blood from the blood vessel enters at least part of sheath 106. In at least one embodiment, sheath 106 is comprised of transparent or translucent material, such as transparent or translucent plastic, rubber, or the like. When using device 100 to access a lumen of a bodily vessel (such as a blood vessel), device 100 may be used to puncture the skin similar to a standard syringe/needle. When needle tip 104 punctures a bodily vessel, a quantity of fluid from the vessel, such as blood in the case of a blood vessel, can then enter the space inside sheath 106 through aperture 200. Because at least part of sheath 106 is transparent or translucent in such an embodiment, a user can visually detect the presence of blood within sheath 106, and can then retract at least part of needle 102 and needle tip 104 within sheath 106 to prevent overperforation.

In at least one embodiment of the present disclosure, such as the embodiment shown in FIGS. 1 and 2, sheath 106 comprises a tapered distal end 110, wherein when needle tip 104 protrudes from sheath 106, needle tip 104 and the tapered distal end 110 of sheath 106 collectively form a relative point, so that when needle tip 104 engages/enters a tissue/vessel, at least part of the tapered distal end 110 of sheath 110 can then also engages/enters the tissue/vessel. Tapered distal end 110 of sheath 106 is also configured to allow blood or other bodily fluids to pass between an outside wall 112 of needle 102 and aperture 200 of sheath 106, so that the blood or other bodily fluid is visible within a lumen 114 of sheath 106.

Protrusion of needle tip 104 from sheath 106 and retraction of needle tip 104 into sheath 106 by way of protractor 108 is facilitated by a needle mechanism 116, such as those mechanisms capable of effectively storing and releasing energy, such as a spring, various compliant polymers, coils, sponges, bladders, and the like, which can comprise various materials such as metals, plastics, polymers (nitinol, for example), for example. Various needle mechanisms 116 of the present disclosure may involve thermo-electrical expansion, whereby an electric current running therethrough may effectively cause needle tip 104 to protract. Protraction, in various embodiments, may be on the order of 0.1 mm-0.2 mm, but could be more or less depending on the application.

As shown in FIGS. 1 and 2, a spring (an exemplary needle mechanism 116) ultimately engages protractor 108 and needle 102, either directly or indirectly, to facilitate movement of needle 102 within sheath 106. For example, and as shown in FIG. 1, when protractor 108 is depressed, needle mechanism 116 causes needle tip 104 to protrude from sheath 106, and when protractor 108 is released, as shown in FIG. 2, needle mechanism 116 causes needle tip 104 to retract within sheath 106. Needle mechanism 116 may be compressed when protractor 108 is engaged as shown in FIG. 1 and may be expanded when protractor 108 is released as shown in FIG. 2 in at least one embodiment, and may be reversed, i.e. expanded when protractor 108 is engaged and compressed when protractor 108 is released, in various other embodiments, depending on the overall configuration of device 100. In at least one embodiment, the spring-loaded needle tip 104 is retractable, and can be advanced or retracted by a linear spring mechanism with a user's fingertip at the proximal end of device 100.

Figure 3:
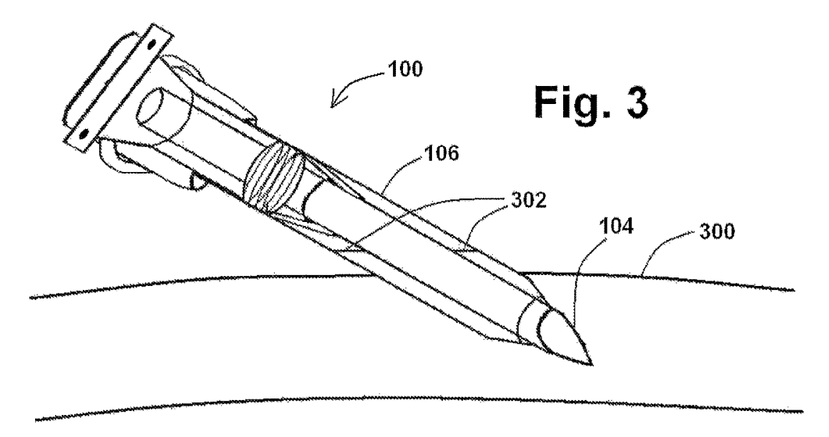
FIG. 3 shows a side view of a device for providing access to a vessel or other luminal organ in a first configuration and at least partially within a bodily vessel, according to at least one embodiment of the present disclosure.

Various devices 100 of the present disclosure can be used, for example, to access the interior of a blood vessel as shown in FIGS. 3 and 4. As shown in FIG. 3, protractor 108 can be depressed or otherwise engaged so that needle tip 104 of device 100 protrudes from sheath 106. A vessel 300 (such as a blood vessel, or other luminal organ within the body) would then be punctured by needle tip 104, and a user of the device 100 would then look for blood or other fluid movement within sheath 106 to indicate access into vessel 300. Upon identification of blood or another fluid within sheath 106, as indicated in FIGS. 3 and 4 by way of fluid level 302, needle tip 104 would be retracted into sheath 106 to prevent overperforation of vessel 300, as shown in FIG. 4. A wire 400 (such as a standard 0.014" guidewire), as shown in FIG. 4 may be advanced through various wire apertures 402 of device 100 and through device 100 so that at least part of wire 400 is positioned within vessel 300.

Figure 5A:
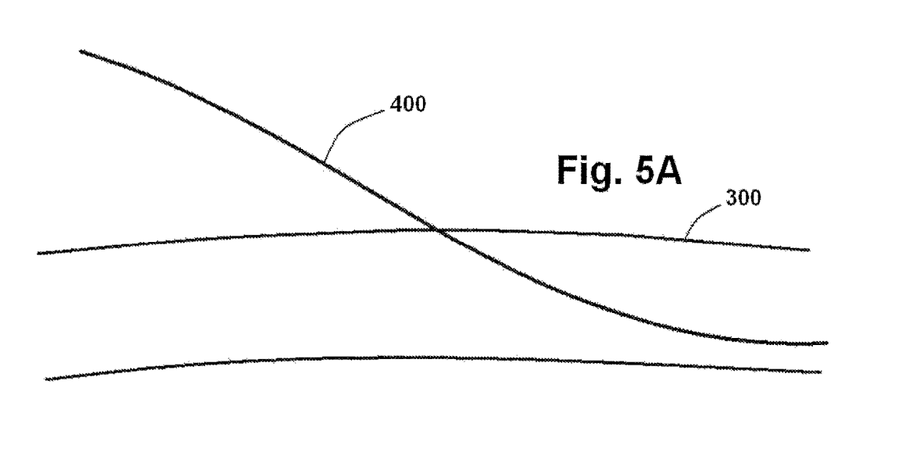
FIG. 5A shows a wire positioned within a bodily vessel after entry using a device for providing access to a vessel or other luminal organ, according to at least one embodiment of the present disclosure.
Figure 5B:
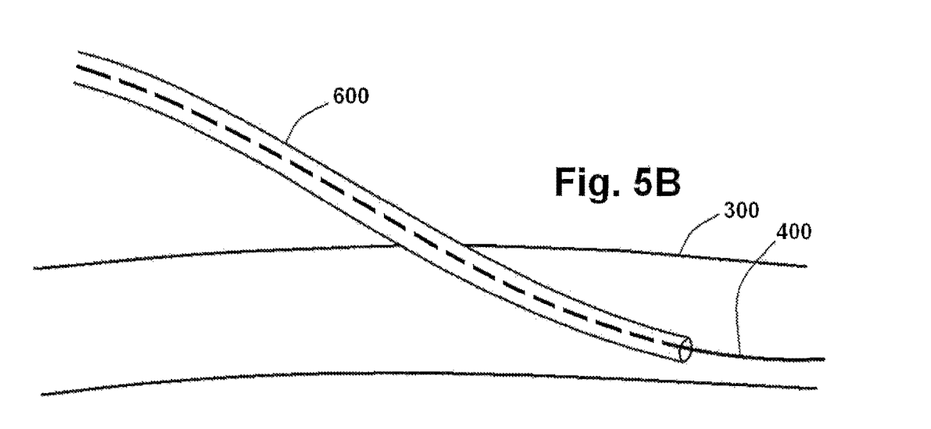
FIG. 5B shows a wire positioned within a bodily vessel with a second device positioned thereon after entry using a device for providing access to a vessel or other luminal organ, according to at least one embodiment of the present disclosure.

All or part of device 100 can then be withdrawn, whereby wire 400 remains with access into vessel 300. In at least one example, and as shown in FIG. 5A, all components of device 100 are removed from vessel, with wire 400 remaining to facilitate entry of any number of wire-fed devices (exemplary second devices 600, such as various catheters, balloon catheters, and/or stents, for example) into vessel 300, as shown in FIG. 5B.

Figure 6A:
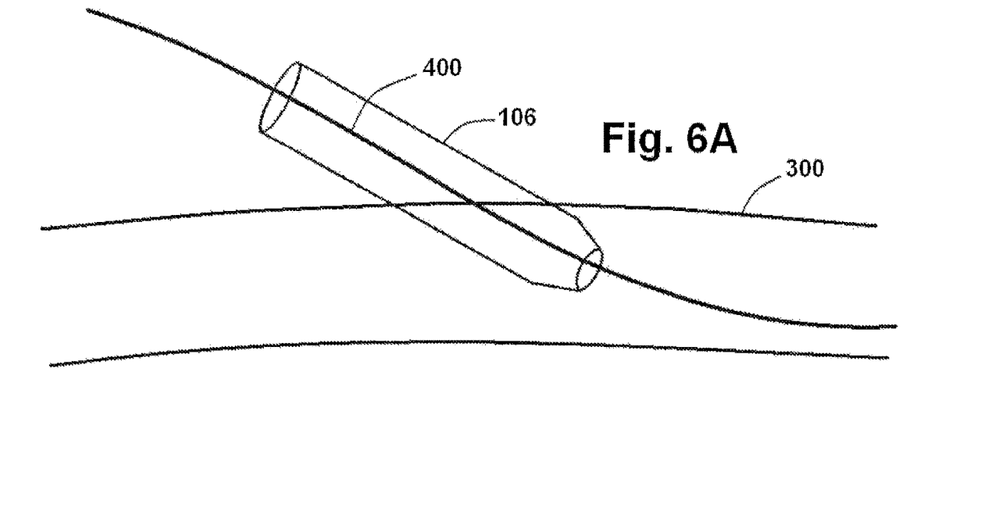
FIG. 6A shows a wire positioned within a sheath within a bodily vessel after entry using a device for providing access to a vessel or other luminal organ, according to at least one embodiment of the present disclosure.
Figure 6B:
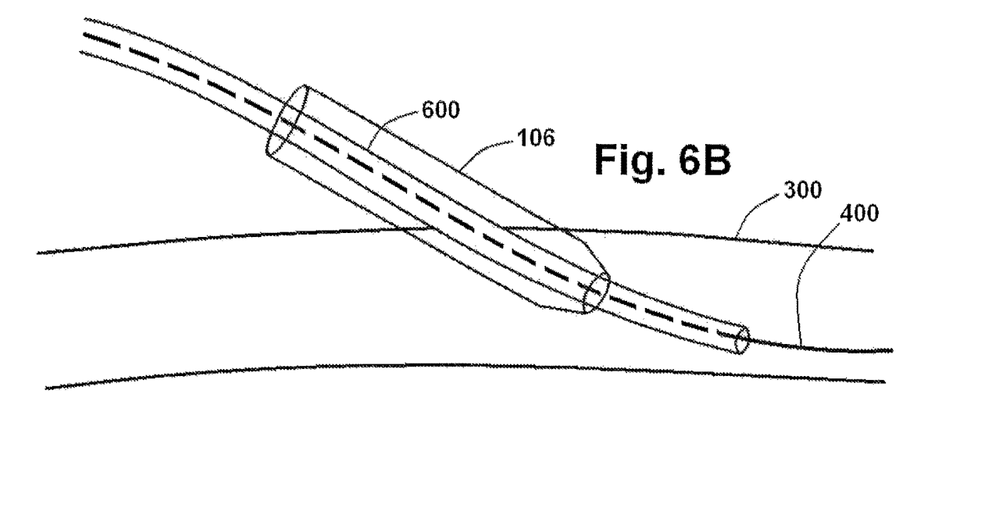
FIG. 6B shows a wire positioned within a sheath within a bodily vessel with a second device positioned thereon after entry using a device for providing access to a vessel or other luminal organ, according to at least one embodiment of the present disclosure.

In at least another example, and as shown in FIG. 6A, at least one component of device 100 may remain to provide access into vessel 300. In at least one embodiment, and as shown in FIG. 6A, sheath 106 can be disconnected from the remainder of device 100, so that when the remainder of device 100 is withdrawn from vessel 300, sheath 106, and optionally wire 400 as shown in FIG. 6A, can remain to provide access into vessel 300. In at least one embodiment, and after device 100 is used to provide access into vessel 300, sheath 106 can be disconnected from the remainder of device 100, the remainder of device 100 can be removed, and then wire 400 can be inserted into sheath 106 so that at least part of wire 400 enters the lumen of vessel 300. One or more second devices 600 can then either be inserted directly into vessel 300 via sheath 106 or advanced over wire 400 positioned within sheath 106 as shown in FIG. 6B.

In various embodiments of devices 100 of the present disclosure, needle 102 is relatively small (having an outer diameter of between about 0.3 mm and 1.0 mm, for example, and an outer diameter of approximately 0.5 mm in at least one embodiment), which is configured to pre-dilate into sheath 106 to allow access of needle tip 104, whereby needle 102 is retractable to provide a blunt non-perforation tip (formed by the tapered distal end 110 of sheath 106 and aperture 200) to prevent overperforation of a vessel 300. In at least one embodiment, needle 102 has an inner diameter of about 0.35 mm. Retraction of needle 102 within sheath 106 transforms device 100 from a puncture device to a sheath. Device 100, in any number of embodiments, can also be used to deliver a substance (fluid, drug, etc.) into a patient's body, and/or used to remove a fluid/substance from the patient.

Figure 7:
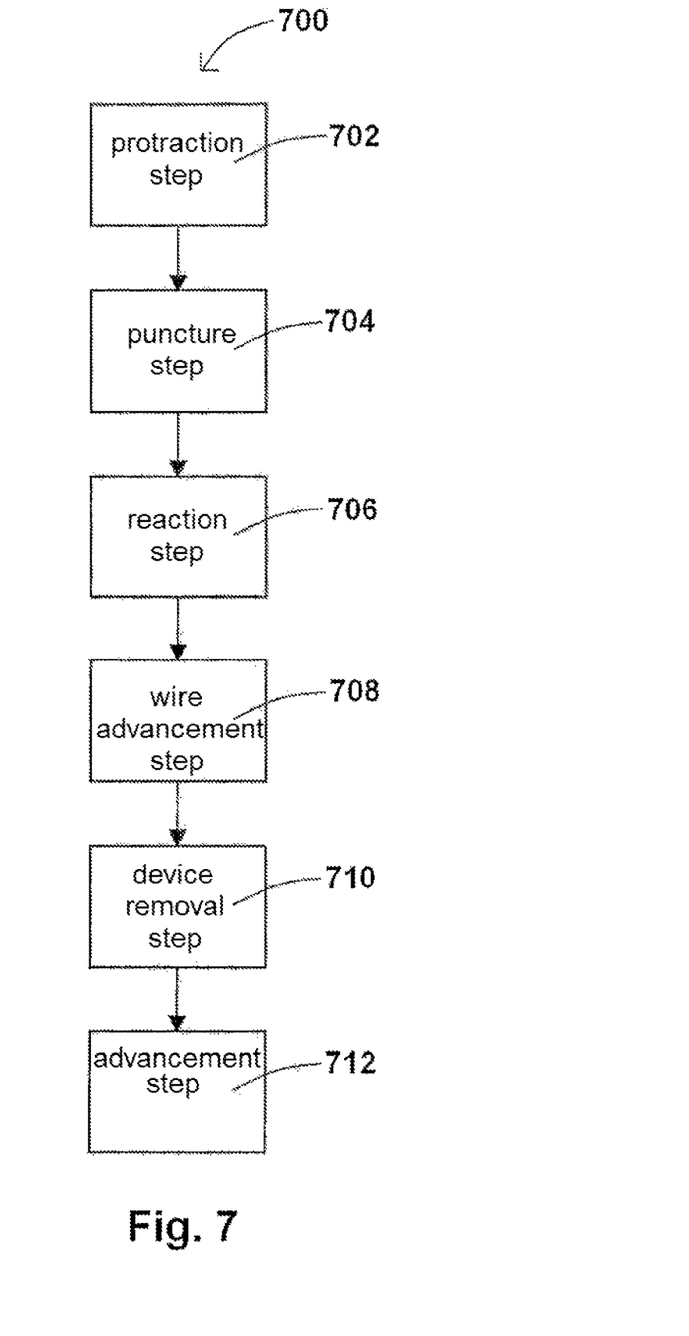
FIG. 7 shows steps of an exemplary method of accessing a mammalian bodily vessel, according to at least one embodiment of the present disclosure.

Steps of an exemplary method of using an exemplary device 100 of the present disclosure to provide access to a bodily vessel are shown in FIG. 7. As shown in FIG. 7, method 700 may comprise the steps of protracting needle tip 104 from sheath 106 (an exemplary protraction step 702), and puncturing a bodily vessel of a patient (such as a radial artery, for example) using needle tip 104 so that needle tip 104 accesses a bodily vessel lumen (an exemplary puncture step 704). An exemplary method 700 further comprises the step of retracting needle tip 104 within sheath 106 to prevent overperforation of the vessel 300 (an exemplary retraction step 706), which, in at least one embodiment, is facilitated by the user identifying movement of a bodily fluid, such as blood, for example, within sheath 106 to indicate device 100 access into a bodily vessel.

In at least one embodiment of a method 700 of the present disclosure, method 700 further comprises the step of advancing a wire 400 through device 100 so that at least part of wire 400 is positioned within the bodily vessel (an exemplary wire advancement step 708). Method 700 may further comprise the optional step of removing all or part of device 100 from the patient so that wire 400 remains (an exemplary device removal step 710). An exemplary method 700 may then further comprise the step of advancing a second device 600 over wire 400 so that at least part of the second device 600 is positioned within vessel 300 (an exemplary advancement step 712). Advancement step 712 may comprise, for example, advancement of a catheter (an exemplary second device 600) to a patient's heart during a heart catheterization procedure. Advancement step 712 may also comprise, for example, advancement of any number of other second devices 600 over wire 400 to access one or more other organs or areas within a patient's body. Various steps of method 700 may be performed manually by a user and/or may be performed automatically as described in further detail herein.

Access to a patient's blood vessel(s) by way of a transfemoral route is most commonly performed, but the present disclosure provides methods of transradial access and devices useful to perform the same. An exemplary device 100 of the present disclosure may be used to provide transradial access to a patient as described below.

Catheterization using a transradial approach involves accessing a relatively small artery in a patient's wrist and the subsequent advancement of a catheter into the patient's heart. As such, transradial access, as referenced herein, involves the general access to a patient's vessel, such as a blood vessel, by way of the patient's wrist. As referenced above and in detail below, transradial access is more difficult to perform than traditional transfemoral access, and various embodiments of devices 100 of the present disclosure can be used with a transradial approach to provide effective access with significantly reduced procedure risk.

Transradial access has several advantages over transfemoral access. First, a patient's upper extremities do not develop as much atherosclerosis as the lower extremities, even with elderly patients, and hence access is always possible. Second, there are no nerves or veins of significant size near the usual site of puncture. Third, the hand's dual arterial supply from the radial and the ulnar artery adds an extra level of safety to the arterial puncture. Hence, if any thrombotic or traumatic arterial occlusion may occur, this usually does not endanger the viability of the hand due to the presence of an adequate collateral blood supply.

In addition, transradial access has significantly less vascular complications when compared to transfemoral access, and allows earlier mobilization of patients post procedure as compared to transfemoral access. Transradial access can also be advantageous in patients with acute coronary syndrome where aggressive antithrombotic and antiplatelet therapy is often instituted, leading to a higher potential for access site bleeding complications with respect to femoral access. Furthermore, patient comfort is increased with early ambulation, and most patients who have undergone cardiac catheterization from both the leg and wrist will strongly prefer the transradial route.

Figure 8:
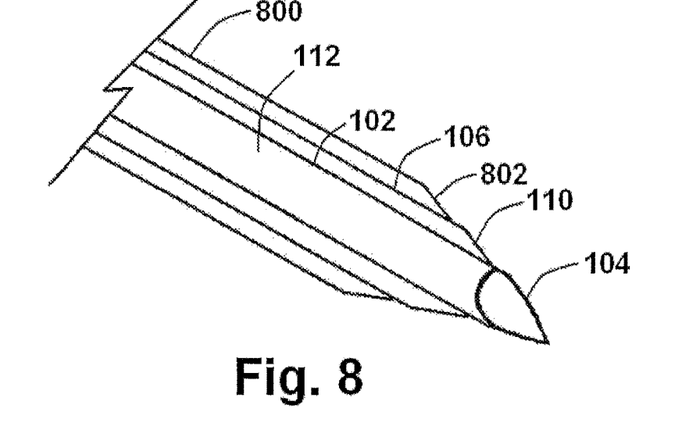
FIG. 8 shows a side view of a portion of a device for providing access to a vessel or other luminal organ having a dilator, according to at least one embodiment of the present disclosure.

In various embodiments of devices 100 of the present disclosure, devices 100 may further comprise a dilator 800. As shown in FIG. 8A, and in at least one embodiment, a portion of device 100 may have a dilator 800 surrounding at least sheath 106, so that insertion of a portion of a device into a vessel 300, as described in detail herein, would also involve the insertion of a distal end 802 of dilator into vessel 300, so that the overall insertion opening is larger than it would have been if the same sheath 106 was inserted into vessel 300 without dilator 800. As shown in FIG. 8A, dilator 800 is larger than sheath 106, and the inherent size/thickness of dilator 800 would provide a larger access opening into vessel 300 as described above. When using embodiments of device 100 having a dilator 800 to access a vessel 300, dilator 800 may be withdrawn along with the remainder of device 100, or all but sheath 106, for example, so that sheath 106 and optionally a wire 400 inserted therethrough remain to provide access into vessel 300.

Additional embodiments of devices 100 of the present disclosure may comprise and/or include one or more features to facilitate automated operation of the same. For example, and in at least one embodiment of a system 900 as shown in FIG. 9, system 900 may comprise one or more portions of an exemplary device 100 and one or more automated features.

Figure 9:
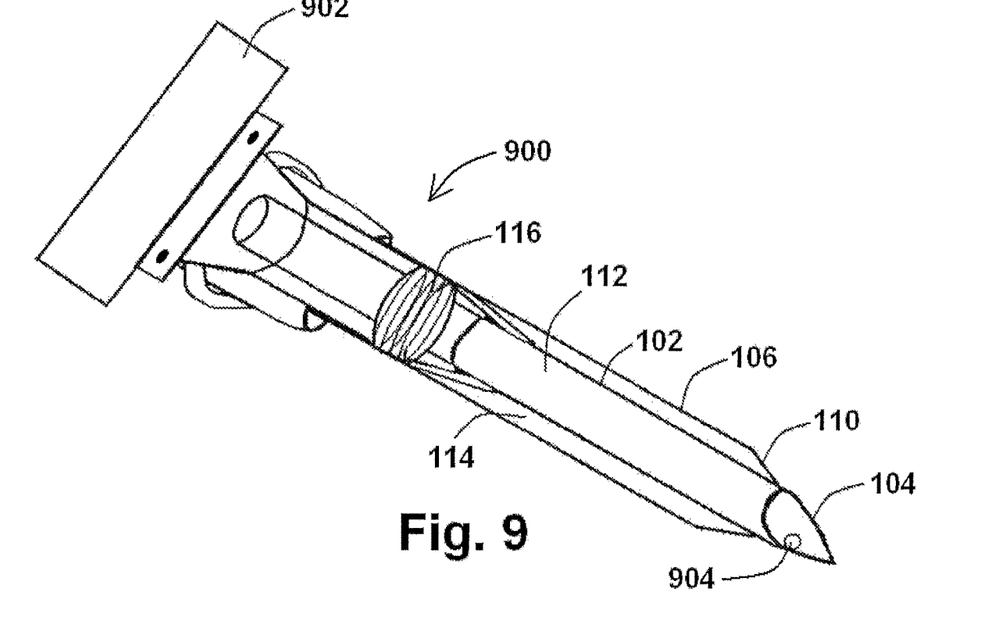
FIG. 9 shows a side view of a system for providing access to a vessel or other luminal organ, according to at least one embodiment of the present disclosure.

As shown in FIG. 9, an exemplary system 900 of the present disclosure comprises a needle 102 having a needle tip 104, a sheath 106, and an actuator 902. Actuator 902, in various embodiments, can be coupled directly to needle 102, or indirectly coupled to needle 102 by way of a needle mechanism 116 and optionally a protractor 108. Actuator 902, in at least one embodiment, is operable to protract and retract needle 102/needle tip 104 from and into sheath 106, and may perform said operation without any direct manual engagement by the user. For example, when a user of system 900 would identify blood or another fluid within sheath 106 after advancement of needle 102/needle tip 104 into a vessel 300 either manually or using actuator 902, the user can operate actuator 902 to retract needle 102/needle tip 104 into sheath 106. In at least one embodiment of system 900 (or use thereof), protraction and retraction occurs automatically by way of actuator 902. In at least one embodiment, actuator 902 can have a first operation to protract needle tip 104, and a second operation to retract needle tip 104.

In various embodiments of systems 900 of the present disclosure, sheaths 106 may not be transparent or translucent as otherwise described herein. For example, and in such an embodiment that would not readily allow a user to visualize blood or another bodily fluid within sheath 106, system 900 may further comprise one or more sensors 904, as shown in FIG. 9, operably coupled to needle 102/needle tip 104 to sense at least one parameter and/or at least one parameter change. Such parameters or parameter changes may include sensing advancement of needle tip 104 through skin, tissue, and a wall of vessel 300 so that needle tip 104 comes into contact with blood within vessel 300. Such sensors 904 may comprise one or more impedance sensors, whereby detected impedance of blood versus tissue, for example, would trigger retraction of needle tip 104 into sheath 106, and/or may comprise one or more oxygen sensors (sensing differences in oxygen concentration from tissues, arteries, and/or veins), lactate sensors (noting different concentrations of lactate in blood versus tissue), or any number of other sensors 904 operable to detect an identifiable parameter within blood and/or another bodily fluid as being different than one or more surrounding tissues/vessels. Such sensors 904 could be electrical, electrochemical, chemo-mechanical, etc., in nature to facilitate the appropriate sensing to trigger advancement and/or retraction of needle 102/needle tip 104 of system 900.

Figure 10:
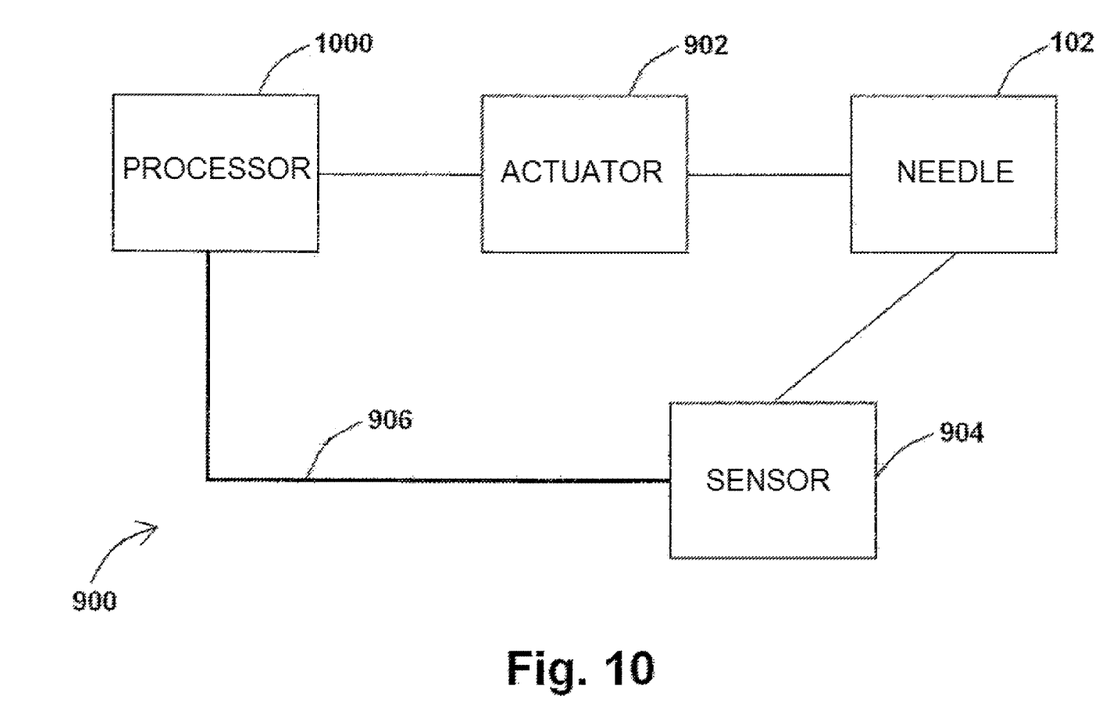
FIG. 10 shows a block diagram of various components of a system for providing access to a vessel or other luminal organ, according to at least one embodiment of the present disclosure.

In at least one embodiment, needle 102/needle tip 104 may itself operate as a sensor given the metallic properties of various embodiments of needles 102. In other embodiments, and as shown in FIG. 10 (discussed in further detail below), one or more sensors 904 are coupled to needle 102 by way of a wire 906, whereby a first portion of wire 906 is coupled to sensor 904, and a second portion of wire 906 is coupled either directly or indirectly to actuator 902. Wire 906, in various embodiments, is operable to carry a signal from sensor 904 to actuator 902, either directly to actuator 902 or indirectly to actuator 902 by way of a processor 1000, referenced below.

A block diagram of various components of portions of an exemplary system 900 of the present disclosure is shown in FIG. 10. As shown in FIG. 10, an exemplary system 900 may comprise an actuator 902, a sensor 904 coupled to needle 102 and/or to processor 1000 by way of a wire 906, whereby processor 1000, actuator 902, and needle 102 are in operable communication with one another. In such an embodiment, for example, actuator 902 could be used to protract needle 102, and when sensor 904 detects a parameter change indicative of vessel 300 access (such as the presence of blood), a signal from sensor is either sent to or received by processor 1000 either through wire 906 or through actuator 902 to processor 1000, for example, so that processor 1000 operates actuator 902 to retract needle 102. Generally speaking, and in at least one embodiment, processor 1000 is operably coupled to sensor 902, wherein processor 1000 is operable to control actuation of actuator 902. In such an embodiment, and when sensor 904 senses a threshold bodily parameter (such as, for example, the presence of blood or a parameter indicative of blood), processor 1000 operates to control actuation of actuator 902 to protract or retract needle 102/needle tip 104. The aforementioned embodiments are merely exemplary in nature, noting that various other components described herein, or differing configurations of components shown in FIG. 10, may be made to facilitate the same or similar end result.

An advantage of the various embodiments of the present disclosure is the enablement of a retractable tip that prevents overperforation of a small vessel. This, in conjunction with a transparent or translucent device wall, provides the doctor with knowledge of the initial perforation as indicated by blood movement in the device. The advanced needle tip can then be retracted to transform the needle into a non-blunt tip sheath which would not perforate the posterior vessel wall.

While various embodiments of devices, systems, and methods for transradial access have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

What is claimed is:

1. A device for providing access to a vessel or other luminal organ and to prevent overperforation of the same, the device comprising:
    a needle having a needle tip and having a sensor coupled to the needle, the sensor operable to detect blood;
    a sheath positioned around at least part of the needle, the sheath defining an aperture at a distal sheath end through which the needle Up can protract, an interior space around the needle positioned therein, and having a tapered distal end configured for percutaneous insertion into a vessel or other luminal organ, wherein at least a portion of a wall of the sheath is comprised of translucent or transparent material;
    a protractor in communication with the whereby engagement of the protractor causes the needle tip to protract from the sheath through the aperture, and whereby release of the protractor causes the needle tip to retract through the aperture into the sheath;
    an actuator in communication with the needle, the actuator configured to facilitate movement of the needle within the sheath while the sheath remains fixed; and
    a processor operably coupled to the actuator, the processor operable to direct operation of the actuator;
    wherein the device is configured so that when the needle tip punctures the vessel or other luminal organ underneath skin after puncturing the skin and is advanced along with the sheath so that the distal sheath end is also positioned within the vessel or other luminal organ and so that fluid within the vessel or other luminal organ is in contact with the needle tip, the fluid can enter the interior space of the sheath directly through the aperture and be visually detected within the sheath through the portion of the sheath wall comprising the translucent or transparent material to indicate that the distal sheath end is positioned within the vessel or other luminal organ;
    wherein the device is further configured and operable to operate the actuator, from directions from the processor, to retract the needle tip of the needle into the aperture of the sheath in response to blood being detected by the sensor so to prevent overperforation of the vessel or other luminal organ; and
    wherein the sheath is detachable from a remainder of the device, and wherein the remainder of the device includes at least the needle, protractor actuator and processor, such that the remainder of the device can be withdrawn from the vessel or other luminal organ without removing the sheath.

2. The device of claim 1, wherein the protractor is selected from the group consisting of a button and a rotatable dial.

3. The device of claim 1, wherein the tapered distal end of the sheath is configured to allow blood or other bodily fluids to pass between an outside wall of the needle and the aperture when the needle is protracted from the sheath.

4. The device of claim 1, further comprising:
    a needle mechanism in communication with the needle and the protractor, the needle mechanism operable to facilitate protraction and retraction of the needle tip from the sheath.

5. The device of claim 4, wherein the needle mechanism is selected from the group consisting of a spring, a compliant polymer, a coil, a sponge, and a bladder.

6. The device of claim 1, further comprising:
    one or more wire apertures defined therethrough, the one or more wire apertures configured to receive a wire.

7. The device of claim 6, further comprising:
    a wire positioned through the one or more wire apertures, the wire configured to permit a second device to be delivered over the wire.

8. The device of claim 7, wherein the wire comprises a guide wire.

9. The device of claim 1, wherein the device comprises part of a system, the system further comprising:
    a dilator configured to surround at least part of the sheath, the dilator further configured for partial insertion into the vessel or other luminal organ;
    a guide wire configured for partial insertion into one of a sheath lumen and a needle lumen, the guide wire further configured for advancement into the vessel or other luminal organ; and an access catheter configured for advancement over the guide wire and further advancement into the vessel or other luminal organ.

10. A system for providing access to a vessel or other luminal organ and to prevent overperforation of the same, the system comprising:
a needle having a needle tip and having a sensor coupled to the needle, the sensor operable to sense at least one bodily parameter;
a sheath positioned around at least part of the needle, the sheath defining an aperture at a distal sheath end through which the needle tip can protract, an interior space around the needle positioned therein, and having a tapered distal end configured for percutaneous insertion into a vessel or other luminal organ, wherein at least a portion of a wall of the sheath is comprised of translucent or transparent material; and
an actuator in communication with the needle, the actuator configured to facilitate movement of the needle within the sheath, whereby a first operation of the actuator causes the needle tip to protract from the sheath through the aperture while the sheath remains fixed, and whereby a second operation of the actuator causes the needle tip to retract through the aperture into the sheath in response to sensor sensing a threshold level of the at least one bodily parameter,
wherein the system is configured so that when the needle Up punctures the vessel or other luminal organ underneath skin after puncturing the skin and is advanced along with the sheath so that the distal sheath end is also positioned within the vessel or other luminal organ and so that fluid within the vessel or other luminal organ is in contact with the needle tip, the fluid can enter the interior space of the sheath directly through the aperture and be visually detected within the sheath through the portion of the sheath wail comprising the translucent or transparent material to indicate that the distal sheath end is positioned within the vessel or other luminal organ so to prevent overperforation of the vessel or other luminal organ; and
wherein the sheath is detachable from a remainder of the system, and wherein the remainder of the system includes at least the needle, sensor, and actuator, such that the remainder of the system can be withdrawn from the vessel or other luminal organ without removing the sheath.

11. The system of claim 10, further comprising:
a needle mechanism in communication with the needle and the actuator, the needle mechanism operable to facilitate protraction and retraction of the needle tip from the sheath.

12. The system of claim 10, wherein the sensor that is coupled to the needle is operable to sense blood.

13. The system of claim 12, wherein the at least one bodily parameter comprises an impedance, an oxygen concentration, and a lactate concentration.

14. The system of claim 12, further comprising:
a wire coupled to the sensor and directly or indirectly coupled to the actuator, the wire capable of transmitting a signal from the sensor to the actuator.

15. The system of claim 12, further comprising:
a processor operably coupled to the sensor, the processor operable to control actuation of the actuator.

16. The system of claim 15, wherein when the sensor senses a threshold bodily parameter, the processor operates to control actuation of the actuator to protract or retract the needle.

17. The system of claim 10, wherein the tapered distal end of the sheath is configured to allow blood or other bodily fluids to pass between an outside wall of the needle and the aperture when the needle is protracted from the sheath.

* * * * *